United States Patent
Song et al.

[11] Patent Number: 5,747,007
[45] Date of Patent: May 5, 1998

[54] DUSTLESS BABY POWDER

[75] Inventors: Jin Song, Bedford; John Koch, Dallas; Marilyn Squier, Garland, all of Tex.

[73] Assignee: Patty Cake, Inc., Dallas, Tex.

[21] Appl. No.: 799,891

[22] Filed: Feb. 13, 1997

[51] Int. Cl.$^6$ ...................................................... A61K 7/06
[52] U.S. Cl. .................................. 424/69; 424/63; 424/65; 424/66
[58] Field of Search .................................. 424/63, 69, 65, 424/66

[56] References Cited

U.S. PATENT DOCUMENTS 4,857,308  8/1989  Fukasawa et al. ........................ 424/63
5,482,702  1/1996  Murphy et al. ........................... 424/65

*Primary Examiner*—Terressa Mosley
*Attorney, Agent, or Firm*—George R. Schultz; Strasburger & Price, L.L.P.

[57] ABSTRACT

A compacted baby powder formulation combines an absorbent with a dry compression agent and a liquid or semi-solid material. The resulting formulation reduces the amount of dispersion of the powdered absorbent. The absorbent can be either an organic or non-organic such as corn starch or talc, respectively. The compression agent can be a microcrystalline cellulose or polyethylene. The liquid or semi-solid can be a ester such as a jojoba ester. The formulation can be augmented with additional additives to provide skin protectant, lubricant or anti-septic benefits.

26 Claims, No Drawings

DUSTLESS BABY POWDER

TECHNICAL FIELD OF THE INVENTION

The present invention relates generally to a compacted baby powder and more specifically to a formulation that reduces the amount of powder that disperses in the air and is wasted or inhaled.

BACKGROUND OF THE INVENTION

Baby powder typically consists of a fine, absorbent material such as talc or corn starch. The powder is stored in a plastic container having a plurality of spaced holes for use in dispensing the powder. A mother will dispense an amount either to her hand which she then pats onto the baby or to the baby directly. In either case, a cloud of powder is produced, with a substantial fraction lost in the air and surrounding area around the baby. There are a growing number of accidental infant deaths each year attributable to the inhalation of air born baby powder.

Unbound powders have less serious drawbacks as well. First, the powders are difficult to accurately apply. As alluded to above, shaking a plastic bottle of powder produces a widely dispersed flow of powder through the air. It tends to spread over a greater area than desired. A second drawback involves the amount of powder wasted. While not very expensive, the wasted powder must still be cleaned up.

A need exists for a compacted powder formula which avoids the disadvantages of unbound powders. Such a compacted powder formula should enable the user to precisely apply the powder. Such a formulation should also minimize the risk of accidental inhalation of the powder by an infant.

SUMMARY OF THE INVENTION

The present invention relates to a compacted baby powder that combines an absorbent with a dry compression agent and a liquid or semi-solid material. The absorbent can be any organic or non-organic absorbent. For example, corn starch is a suitable organic absorbent, while talc or kaolin is a suitable non-organic absorbent. The dry compression agent allows the absorbent to be compacted. A suitable compression agent is microcrystalline cellulose or oxidized polyethylene. Finally, the liquid or semi-solid material can be any liquid or semi-solid emollients or humectants and can also aid in the compaction of the product. For example, a jojoba ester is a suitable liquid material.

In addition to these three basic elements, the formulation can be augmented with other ingredients which have proven beneficial effects on the skin. For example, zinc oxide can be included to help treat diaper rash. Lauroyl lysine can be added as a skin lubricant. Benzenthonium chloride can be added as an anti-septic. Alpha hydroxy acid could be added to improve the texture of the treated skin. For each example given, a number of other ingredients could be substituted. The final formulation though, has the benefits of an absorbent without the additional waste or risk associated with prior art powders.

DETAILED DESCRIPTION OF THE INVENTION

The present compacted powder formulation overcomes many of the disadvantages found in the prior art. As discussed above, the formulation consists of three basic ingredients: an absorbent, a dry compression agent, and a liquid or semi-solid material. The absorbent can be any organic or non-organic absorbent. The preferred absorbents are talc, kaolin, and corn starch. Alternative absorbents can be wheat starch, oat starch, clay flour and chalk. The absorbent represents between 10% to 95% of the formulation.

The dry compression agent is preferably a microcrystalline cellulose. However, a micronized polyethylene or micronized oxidized polyethylene or combination of compression agents can also be used. Stearates or fatty acid derivatives can be used as compression agents as well. For example, zinc stearate, calcium stearate, or magnesium stearate can be used. The compression agent increases the overall hardness of the powder tablet. The compression material represents between 5% to 60% of the formulation. The liquid material is preferably a jojoba ester, however, it can be any ester or oil. Other suitable liquids could be propylene glycol, silicone, polyol, organic alcohol, organic acid, or organic ether. Indeed, a semi-solid with a low-temperature melting point could be used. Liquid emollients or humectants could be used. The liquid material represents between 2% to 35% of the formulation.

The preferred composition is approximately 62% talc, 25% microcrystalline cellulose, 7% oxidized polyethylene and 6% jojoba ester. A small amount of fragrance can be added. Also, zinc oxide can be included to help treat diaper rash. Also, as discussed above, other beneficial ingredients can be added to the formulation to treat the complexion of the skin. The formulation, while suitable for baby powder, can also be applied to adult skin. Lauroyl lysine can be added as a skin lubricant. Benzenthonium chloride can be added as an anti-septic. Alpha hydroxy acid could be added to improve the texture of the treated skin.

Although preferred embodiments of the present invention have been described in the foregoing Detailed Description and illustrated in the accompanying drawings, it will be understood that the invention is not limited to the embodiments disclosed, but is capable of numerous rearrangements, modifications, and substitutions of parts and elements without departing from the spirit of the invention. Accordingly, the present invention is intended to encompass such rearrangements, modifications, and substitutions of parts and elements as fall within the scope of the appended claims.

We claim:

1. A dustless baby powder comprising:
   (a) absorbent;
   (b) a compression agent; and
   (c) a liquid or semi-solid wherein the compression agent diminishes the dispersiveness of the absorbent.

2. The compacted baby powder of claim 1 further comprises a fragrance.

3. The compacted baby powder of claim 1 further comprises an active ingredient to treat a rash.

4. The compacted baby power of claim 1 further comprises an active ingredient to provide anti-septic action.

5. The compacted baby power of claim 1 further comprises a skin conditioning, lubricating or soothing action.

6. The compacted baby powder of claim 1 wherein said absorbent is an organic absorbent.

7. The compacted baby powder of claim 6 wherein said organic absorbent is a corn starch.

8. The compacted baby power of claim 6 wherein said organic absorbent is a flour.

9. The compacted baby powder of claim 1 wherein said absorbent is a non-organic absorbent.

10. The compacted baby powder of claim 9 wherein said non-organic absorbent is a talc.

11. The compacted powder formulation of claim 9 wherein said non-organic absorbent is a kaolin.

12. The compacted baby power of claim 9 wherein said non-organic absorbent is a clay.

13. The compacted baby powder of claim 1 wherein said formulation comprises between 10% and 95% absorbent.

14. The compacted baby powder of claim 1 wherein said compression agent comprises a microcrystalline cellulose.

15. The compacted baby powder of claim 1 wherein said compression agent comprises a polyethylene.

16. The compacted baby power of claim 1 wherein said compression agent comprises a fatty acid derivative.

17. The compacted baby powder of claim 1 where said formulation comprises between 5% and 60% compression agent.

18. The compacted powder of claim 1 wherein said compression agent comprises a mixture of two or more compression agents.

19. The compacted baby powder of claim 1 wherein said liquid or semi-solid comprises an ester.

20. The compacted powder of claim 1 wherein said liquid or semi-solid comprises an oil.

21. The compacted power of claim 1 wherein said liquid or semi-solid comprises a silicone.

22. The compacted baby powder of claim 1 wherein said liquid or semi-solid comprises a polyol.

23. The compacted baby powder of claim 1 wherein said liquid or semi-solid comprises an organic alcohol.

24. The compacted baby powder of claim 1 wherein said liquid or semi-solid comprises an organic acid.

25. The compacted baby powder of claim 1 wherein said liquid or semi-solid comprises an organic ether.

26. The compacted powder of claim 19 wherein said ester is a jojoba ester.

\* \* \* \* \*